United States Patent [19]

Overhults

[11] 3,940,362

[45] Feb. 24, 1976

[54] CROSS-LINKED CYANOACRYLATE ADHESIVE COMPOSITIONS

[75] Inventor: Wendell C. Overhults, East Brunswick, N.J.

[73] Assignee: Johnson & Johnson, East Brunswick, N.J.

[22] Filed: May 25, 1972

[21] Appl. No.: 257,036

[52] U.S. Cl. ........ 260/42.16; 260/42.29; 260/42.52; 260/85.5 A; 260/85.5 ES; 260/86.1 N
[51] Int. Cl.² C08F 236/12; C08K 3/20; C08K 3/36; C08L 35/04
[58] Field of Search...... 260/41 A, 41 B, 87.7, 92.1, 260/998.11, 85.5 A, 85.5 ES, 86.1 N, 42.16, 42.29, 42.52

[56] References Cited

UNITED STATES PATENTS

| | | | |
|---|---|---|---|
| 2,558,139 | 7/1951 | Knock | 260/45.5 |
| 2,833,753 | 4/1958 | Lal | 260/89.5 |
| 3,442,851 | 5/1969 | McManimie | 260/41 A |
| 3,527,729 | 1/1971 | Bingham et al. | 260/37 |
| 3,539,533 | 11/1970 | Lee | 260/47 |
| 3,663,501 | 4/1972 | Adams | 260/41 R |

FOREIGN PATENTS OR APPLICATIONS 1,122,439   7/1968   United Kingdom

Primary Examiner—Allan Lieberman

[57] ABSTRACT

New polymerizable adhesive compositions comprising a monomeric ester of α-cyanoacrylic acid and a difunctional monomeric cross-linking agent which is a diester of acrylic or methacrylic acid and an alcohol having at least two esterifiable hydroxyl group, are found to develop increased cohesive bond strength upon polymerization. The compositions, if desired, can contain a finely divided aggregate, preferred aggregates being alumina and quartz. In addition, the compositions can advantageously contain sodium fluoride.

The monomeric compounds of these adhesive compositions are polymerized in a cross-linked mode by means of an amine activated free radical initiator.

The compositions can be applied to either wet or dry surfaces of a variety of materials. They are suitable for application to animal tissue, e.g., bone and flesh, and are particularly suitable for the treatment of teeth, such as for use as temporary fillings, the preparation of dental restorations and especially for filling and sealing pits and fissures in prophylactic dentistry.

19 Claims, No Drawings

CROSS-LINKED CYANOACRYLATE ADHESIVE COMPOSITIONS

FIELD OF THE INVENTION

This invention relates to new and novel polymerizable adhesive compositions. In particular, this invention relates to compositions comprising a monomeric ester of α-cyanoacrylic acid and a difunctional monomeric cross-linking agent which is a diester of acrylic or methacrylic acid and a polyfunctional alcohol having at least two esterifiable hydroxyl groups. These compositions have been found to be particularly useful in the treatment of teeth.

The compositions of this invention also include those which in addition comprise, either alone or in combination, a finely divided aggregate or filler, such as alumina or quartz; and sodium fluoride as an adhesive bond enhancing material.

While the compositions of this invention are in particular described in connection with those embodiments that are primarily designed for use in the treatment of teeth, it should be understood that the compositions of this invention are not limited to such application. These compositions can be utilized for filling or bonding various other materials including, for example, animal tissue such as bone, flesh, skin and the like and also such porous and nonporous materials as ceramics, glass, metal, wood and plastics together with joining or filling other materials where the unique properties of the present composition can be advantageously employed as will be apparent to those skilled in the art upon reading this disclosure.

DESCRIPTION OF THE PRIOR ART

Monomeric ester of α-cyanoacrylic acid are well known for use as adhesives. Upon polymerization, such compositions have been utilized to join a variety of materials, and such compositions and uses therefor are described in U.S. Pat. No. 2,794,788. In addition, U.S. Pat. No. 3,663,501, describes the use of compositions comprising esters of α-cyanoacrylic acid for use in the treatment of teeth.

Many individuals have imperfections in the enamel layer of their teeth, which imperfections are a potential site for the development of caries, especially if dental hygiene is less than complete. Such imperfections are most often found on the occlusive surfaces of the teeth. These imperfections are known as pits and fissures, and heretofore known compositions incorporating esters of α-cyanoacrylic acid have been utilized in dentistry to seal such pits and fissures. The pit and fissure sealant composition is applied in the fluid state to the occlusive surfaces of cleaned teeth. Upon curing in situ there is provided a protective layer which seals the imperfections and discontinuities in the enamel layer, which otherwise could permit bacteria to attack enamel and initiate decay. Unless dental care is made available, such decay will ultimately destroy the tooth structure.

Unfortunately, these linearly polymerized alkyl 2-cyanoacrylates, while having excellent adhesion to tooth surfaces do not develop an exceptionally high cohesive strength. Such cohesive strength is desirable to enable the cured sealant to withstand, over an extended period, the grinding action and pressures experienced during mastication.

Furthermore, compositions heretofore utilized as dental restoratives, i.e., materials used to fill prepared cavities, have a tendency to shrink from the walls of the tooth surface. This shrinkage is not only encountered with plastic filling compositions, e.g., silver amalgams, but also with adhesives used to cement gold inlays in place. Whereever this shrinkage occurs, it creates a void between the filling material and the inner surface of the tooth. usually this void occurs at the base of the filling, so no channel communicates to the outer surface of the tooth. If a channel does communicate to the outer surface of the tooth, it presents an opportunity for fresh decay to occur. Dentistry has long sought materials that have improved adherence to tooth surfaces without shrinking therefrom, since such materials would simplify procedures now employed when preparing a tooth for receiving a restorative to minimize the likelihood of new decay forming under the filling.

Therefore, the general object of this invention is to provide adhesive compositions comprising α-cyanoacrylate esters having improved cohesive bond strength.

Another object of this invention is to provide compositions for both dental prophylaxis and dental restorations which adhere to teeth with a strong adhesive bond and have at the same time, an improved cohesive bond strength.

It is a still further object of this invention to provide a composition for use as pit and fissure sealant that has improved cohesive strength to enable it to better withstand the grinding forces which teeth undergo.

A still further object of this invention is to provide a composition which, when used as a dental restorative, will resist shrinking from tooth surfaces to a remarkable degree.

SUMMARY OF THE INVENTION

The adhesive composition of this invention which achieves the foregoing objects and advantages comprises a cement portion comprising a blend of a monomeric ester of α-cyanoacrylic acid and a difunctional monomeric crosslinking agent which is a polyfunctional alcohol having at least two esterifiable hydroxyl groups. To initiate polymerization there is added to the monomer blend, a catalytic amount of an amine activated free radical initiator. After a short period of time, referred to as the transition time, the material begins to become more viscous and usually within one or two minutes thereafter, it hardens. It has additionally been found that the wear properties of the adhesive composition can be improved by the addition to the cement portion of a finely divided filler or aggreagte. The preferred aggregates are quartz and alumina, and additionally, finely divided sodium fluoride can be added to achieve enhanced aehesive bond strength.

After initiation, the material can be worked onto whatever surfaces are to be filled, e.g., teeth, or onto pieces or parts that are to be joined. The increased viscosity after transition enables one to more easily contain the material within a desired space.

DETAILED DESCRIPTION OF THE INVENTION

The cement portion of the adhesive composition of this invention comprises a blend of two monomers.

The first monomer is a monofunctional ester of α-cyanoacrylic acid having the formula:

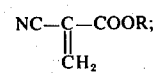

where R is a branched or straight chain alkyl group of from 1 to 16 carbon atoms; cyclohexyl; or phenyl. As stated previously, such esters are described in U.S. Pat. No. 2,794,788.

The ester of α-cyanoacrylic acid can comprise from 5 to 95% of the cement portion, yet the desired amount to include is from about 20 to 80% by weight. If used in an amount of less than 20%, the adhesive bond strength of the cured cement is diminished, and when used in amounts greater than 80%, the sought after cohesive bond strength is not entirely achieved. Generally, the adhesive properties of the cement appear to be maximized when about 60% by weight of the alkyl-α-cyanoacrylate ester is included.

The preferred monomer, as more fully described in the specific illustrative examples which follow, is isobutyl-α-cyanoacrylate.

The second monomer in the cement portion is a difunctional monomer which is an ester of acrylic or methacrylic acid and a polyfunctional alcohol having at least two esterifiable hydroxyl groups. Such compounds are exemplified by the formula

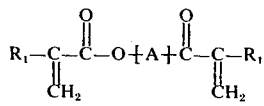

wherein $R_1$ is methyl or hydrogen; A is $-R_2 + O \frac{}{n}$ where $R_2$ is methylene, ethylene, propylene, isopropylene, butylene and isobutylene and $n$ is an integer of from 1 to 3; or

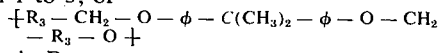

wherein $R_3$ are

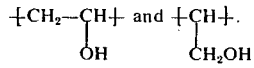

In the above formula only ester and ether bonds through oxygen are contemplated, and no peroxy bonds are implied.

Specific examples of such monomers include: bisphenol A diglycidyl dimethacrylate (Bis-GMA) ethylene glycol dimethacrylate and diacrylate, diethyleneglycol dimethacrylate and diacrylate, triethyleneglycol dimethacrylate and diacrylate, 1,3 propanediol dimethacrylate and diacrylate, 2,2 dimethyl propane diol diacrylate, tripropylene glycol dimethacrylate and diacrylate and 1,3 butylene glycol dimethacrylate and diacrylate.

The amount of difunctional monomer in the cement portion can vary between 95 and 5% by weight. Generally, as dictated by the more suitable quantities of the monofunctional monomer present, the difunctional monomer will be present in a quantity of from 80 to 20% by weight. The preferred quantity is 40% by weight especially when the preferred difunctional monomer, 1,3-butylene glycol dimethacrylate, is employed.

The catalyst system for initiating polymerization of the cement portion consists of a free radical catalyst in combination with an amine activator for that catalyst.

These amine activators comprise any of the basic amine compounds having a $pK_b$ in water of 1 to 12 and in which no nitrogen has more than one attached group exceeding five carbons. The $pK_b$ value is determined in accordance with the procedure set forth by N. F. Hall and M. R. Sprinkle, American Chemical Society, 54 3469(1932). The amine must not have more than one substituent group as bulky as a hexyl or phenyl group.

Illustrative of suitable amines are N,N-dimethyl-p-toluidine and N,N-dimethylaniline, N,N-diethylaniline, N-methylbenzylamine, triethanolamine, diethanolamine, 2-picoline, 4-picoline, tributylamine, 4-ethylpyridine, pyridine, N,N-diethyl-1-napthylamine, hexamethylenediamine, N,N-diethylethylenediamine, preferably N,N-dimethyl-p-toluidine, N,N-dimethylaniline, and N,N-di-β-hydroxyethyl-p-toluidine, the latter being preferred.

The free radical catalyst is preferably a peroxy compound such as those commonly used to effect initiation of polymerization reactions that proceed by means of a free radical mechanism. Examples of such catalysts include aromatic peroxides, including benzoyl peroxide and cumyl peroxide, benzoyl peroxide being preferred.

It is suitable that the free radical catalyst be employed in a quantity of from about 2–15 parts by weight for each hundred parts by weight of the total cement portion.

The quantity of amine activator utilized can vary over a wide range, and in general, it has been found that the quantity of the amine activator employed can vary between 5 and 150 mole percent of the free radical catalyst without deleterious results. Furthermore, when using the preferred activator, N,N-di-β-hydroxyethyl-p-toluidine, it is likewise preferred that an equal molar amount of that amine activator be used compared to the molar amount of the free radical catalyst employed. However, when using faster acting activators such for example, N,N-dimethyl-p-toluidine, it is advisable to either use less of the amine activator or to include in the α-cyanoacrylic acid ester a small portion of an amine activator inhibitor such for example as a Lewis acid, e.g., boron trifluoride or the like.

otherwise, the reaction may proceed so rapidly by an anionic mechanism, that only a small portion of the material will be cross-linked. The proper amount of amine activator can be selected with only slight experimentation. Generally, this can be estimated in two ways. If the transition time is less than 10 seconds and hardening occurs prior to 50 seconds at room temperature, the activity of the amine activator predominates too much and should be diminished either by reducing the amount thereof or including an amine activator inhibitor. Also the activity of the amine activator is deemed too pronounced if a large portion of the polymerized material is soluble in acetone, which solubility indicates at least qualitatively, the degree of cross-linking. Therefore, if the polymerized material is too acetone soluble, the quantity or activity of the amine activator should be diminished.

The pre-polymerized composition of this invention, at the time immediately proceeding reaction, thus comprises a cement portion comprising the monofunctional monomer and the difunctional monomer and a catalyst portion comprising the free radical catalysts and an amine activator therefor.

Because contact of the amine activator with the monofunctional monomer will initiate polymerization, it is essential that such contact not occur until polymerization is desired. On the other hand, the free radical catalyst, in the absence of ultra-violet light or extreme heat remains quiescent until the reaction mixture becomes warmed by the heat of reaction upon initiation with the amine activator.

Therefore, in order to stabilize the elements of the composition of this invention during storage and yet allow the polymerization step to proceed in a direct, straight-forward manner without cumbersome mixing it is an aspect of this invention that a prepolymer blend comprising a separated two component system be provided.

Such two component systems can comprise:

| | COMPONENT | |
|---|---|---|
| | I | II |
| A | amine activator + difunctional monomer | free radical catalyst + monofunctional monomer |
| B | amine activator + free radical catalyst + difunctional monomer | monofunctional monomer |
| C | amine activator + free radical catalyst | monofunctional monomer + difunctional monomer |

Although the above components when admixed and polymerized result in excellent adhesives for pit and fissure or other applications, it is sometimes desirable to include a finely divided solid filler or aggregate in the composition.

Any finely divided solid, e.g., from about 1–100 microns, which is inert to the monomers can be utilized. Suitable fillers include polyethylene fused silica, quartz, and aluminum oxide (alumina). Alumina is presently preferred for most purposes. The filler is present in amounts of about 1 to 4 parts by weight of filler for each part by weight of the combined cement and activated catalyst portions.

Where the cement is to be used as a dental cement, resistance to abrasion and wear is an important factor as is adherence to tooth structure. it has been found that resistance to wear or abrasion and adherence to tooth structure are substantially improved by employing the blend of particles set forth in my co-pending application Ser. No. 241,377, filed Apr. 5, 1972.

Thus, when employing preferred fillers, e.g., alumina and quartz, the mix preferably contains about equal parts by weight of the 40–50 micron and 90–100 micron size particles.

If the inclusion of a finely divided filler in the polymerized composition is deemed desirable, this filler can be added separately, or combined with one of the prepolymer components. In either case, it can also be utilized to carry the free radical catalyst or the amine activator, or both.

In order to add one or both of the catalysts to the filler any inert readily evaporable solvent may be used to dilute the catalyst to insure complete admixture of the filler.

Preferred solvents are, for example, organic compounds such as lower boiling ketones and aliphatic and aromatic hydrocarbons. The catalyst containing solution is added in small amounts while stirring to assure a uniform coating. The amount of catalyst added depends on the particular polymerization time required. Preferably, the amount of catalyst present in the cement composition is in the range of about 3–8% by weight of free radical catalyst based on the weight of the cement portion, and 5.0 to 150 mole percent of the amine activator based on the quantity expressed in moles of the free radical catalyst employed.

With certain fillers such as quartz and alumina, particularly alumina, the effectiveness of an amine anionic catalyst, after addition thereof to the filler, is dissipated relatively rapidly. This dissipation can be overcome by applying to the filler, an under-coating of a trialkoxysilyl compound as taught in my co-pending application U.S. Ser. No. 719,662 filed Apr. 8, 1968. The preferred non-catalytic trialkoxysilyl compounds are: gamma-glycidoxypropyltrimethoxysilane and gamma-methacryloxypropyltrimethoxysilane.

If pretreatment with the non-catalytic trialkoxysilyl compound is indicated, the filler is first treated with a solution of the trialkoxysilyl compounds in a solvent. Any solvent nonreactive with respect to the trialkoxysilyl compound and which can readily be removed by evaporation may be employed, the preferred solvents being organic compounds such as those mentioned above for adding the amine activator. The treating solution should contain at least about 5% by weight of the trialkoxysilyl compound, preferably at least about 10%, the upper limit for satisfactory results being in the range of about 60%. After treatment with the solution of silyl compound the filler is dried by conventional means and then treated with a solution of the amine activator, as above described.

As previously indicated, the adhesive compositions of present invention can include sodium fluoride in amounts of about 5% to 25% by weight of the total finely divided filler, cement, and catalyst portions of the composition, preferably about 10 to 20%. The sodium fluoride may supplement the filler or replace a portion thereof. When added, the sodium fluoride should generally have a particle size in the range of about 10 to 100 microns.

When the adhesive cement is intended for use in dental applications, it may be desirable in some instances to add the usual tinting substances that are utilized in dentistry. If no more than 0.15% by weight of the total composition including cement and catalyst portions and fillers including sodium fluoride, no interference with activation is encountered. The use of a larger amount is usually not necessary, especially when the translucent quartz filler is included, because the quartz filler imparts the natural tooth color to the pit and fissure sealant or dental restoration.

If carbon is utilized as a tinting agent it is best employed in a concentration of less than 0.15% and if an activated carbon, less than 0.10% should be included so as not to interfere with the action of the amine activator.

In a preferred embodiment, the amine activator is dissolved or suspended in the difunctional monomer to form one component of the two component system referred to as A above. The other component comprising the free radical catalyst and the monofunctional monomer is likewise prepared. The two components are kept separate until polymerization is desired. At that time, the two components are admixed and the polymerization reaction proceeds at room temperature without any additional heating.

When a filler is utilized it can either be preblended into component I or II, or be added as a separate component. if the filler has been treated to carry the amine activator it can only be preblended with component I and can not of course be preblended with component II, since the amine activator contained thereon would prematurely polymerize the monofunctional monomer.

The preferred embodiment comprises in component I and admixture of 4.20% N,N-di-β-hydroxyethyl-p-toluidine dissolved in 36.32% 1-3-butyleneglycol dimethacrylate, while component II comprises 5.00% benzoyl peroxide dissolved in 54.48% isobutyl-2-cyanoacrylate, all percentages here expressed in weight percent of the total composition. When the two components are admixed, setting into a hard impervious mass occurs approximately 55 seconds after admixing at room temperature.

For a short time after setting, the surface of the mass is slightly tacky. This is not believed objectionable or pronounced in the preferred embodiment. Yet, if objectionable, this tackiness can be overcome by the addition of a filler.

When used as a pit fissure sealant the fluid admixture of components I and II are applied in the usual manner of known pit and fissure sealants to prepared teeth. When employed as a dental restorative, it can be used analogously to as other plastic filling materials, except after packing the prepared tooth cavity, any excess must be removed before setting occurs, since adherence to teeth is so strong that the usual chipping techniques cannot easily be used.

Now, having described the invention, the following examples are set forth by way of illustration.

EXAMPLE I

A composition comprising 5.00% benzoyl peroxide; 4.20% N,N-dimethyl-p-toluidine; 72.64% isobutyl-2-cyanoacrylate; and 18.16% 1,3-butyleneglycol dimethacrylate all percentages by weight is prepared as follows. The benzoyl peroxide is dissolved in the isobutyl-2-cyanoacrylate and separately the N,N-dimethyl-p-toluidine is dissolved in the 1,3-butyleneglycol dimethacrylate. The two admixtures are combined and harden into a cohesive mass.

EXAMPLE II

A composition similar to Example I, except containing 54.48% isobutyl-2-cyanoacrylate and 36.32% 1,3-butylene-glycol dimethacrylate is prepared as set forth in that Example and upon admixture of the separate components it hardened into a cohesive mass.

EXAMPLE III

A composition similar to Example I, except containing 36.32% isobutyl-2-cyanoacrylate and 54.48% 1,3-butylene-glycol dimethacrylate is prepared as set forth in that Example and upon admixture of the separate components it hardened into a cohesive mass.

EXAMPLE IV

A composition similar to Example I, except containing 18.16% isobutyl-2-cyanoacrylate and 72.64% 1,3-butylene-glycol dimethacrylate is prepared as set forth in that Example and upon admixture of the separate components it hardened into a cohesive mass.

In the above Examples the transition time (the elapsed time between when the material becomes too thick to apply to a surface and the time the material becomes completely hard) is less than 30 seconds.

EXAMPLES V — XVII

Examples I through IV are repeated using the following difunctional monomers in place of the 1,3-butylene-glycol dimethacrylate.
bisphenol A diglycidyl dimethacrylate;
1,3-butyleneglycol diacrylate;
ethyleneglycol dimethacrylate;
ethyleneglycol diacrylate;
diethyleneglycol dimethacrylate;
diethyleneglycol diacrylate;
1,3-propanediol dimethacrylate;
1,3-propanediol diacrylate;
2,2-dimethyl propanediol diacrylate;
tripropyleneglycol dimethacrylate;
tripropyleneglycol diacrylate;
triethyleneglycol diacrylate; and
triethyleneglycol dimethacrylate.

EXAMPLES XVIII — XXVI

Examples I—XVII are repeated using the following monomers in place of the isobutyl-2-cyanoacrylate.
methyl-2-cyanoacrylate;
ethyl-2-cyanoacrylate;
propyl-2-cyanoacrylate;
n-butyl-2-cyanoacrylate;
n-amyl-2-cyanoacrylate;
isoamyl-2-cyanoacrylate;
n-hexyl-2-cyanoacrylate;
n-heptyl-2-cyanoacrylate; and
n-octyl-2-cyanoacrylate.

The substitution of N,N-di-$\beta$-hydroxyethyl-p-toluidine for N,N-dimethyl-p-toluidine generally gives a more cross-linked product as shown by obtaining only a trace amount of soluble polymer on extraction with refluxing acetone.

EXAMPLE XXVII

A composition comprising 75% alumina (50%—150 grit and 50%—320 grit coated with 5% $\alpha$-methacryloxypropyl trimethoxysilane and carrying 2.3% by weight benzoyl peroxide) and 25% monomers and anionic catalyst (60% isobutyl-2-cyanoacrylate and 40% 1,3 butyleneglycol dimethacrylate containing 10% N,N-dimethyl-p-toluidine) is prepared as follows. The alumina was admixed with the isobutyl-2-cyanoacrylate and this then combined with the 1,3-butyleneglycol dimethacrylate containing the anionic catalyst. The admixture then hardened completely in 70 seconds with a transition time of less than 10 seconds. This was repeated using 90:10, 80:20, 50:50, 40:60 and 20:80 mixtures of the isobutyl-2-cyanoacrylate and 1,3-butyleneglycol dimethacrylate. The material upon hardening has good adhesion as shown by the effort required to snap apart steel sheets bonded together with the above compositions.

The representative compression strength developed is as follows.

| isobutyl-2-cyanoacrylate/<br>1,3-butyleneglycol dimethacrylate | Compression<br>Strength |
| --- | --- |
| 90/10 | 9,940 |
| 80/20 | 12,940 |
| 60/40 | 14,870 |
| 50/50 | 17,900 |
| 40/60 | 20,750 |
| 20/80 | 23,000 |

EXAMPLE XXVIII

In the composition of Example XXVII the quantity of alumina is reduced to 50%, the monomer content increased to 33⅓% and 16⅔% sodium fluoride added. The sodium fluoride is admixed with the isobutyl-2-cyanoacrylate after the addition of the alumina and then the first monomer component comprising the alumina, the sodium fluoride and the isobutyl-2- cyanoacrylate is admixed with the second component containing the 1,3-buytyleneglycol dimethacrylate and the N,N-dimethyl-p-toluidine.

In using the compositions of the foregoing examples as pit and fissure sealants, the patient's mouth is first rinsed with an oral antiseptic and then with water. The teeth are isolated with cotton rolls then thoroughly dried with an air syringe and etched for approximately one minute with phosphoric acid. The patient then rinses his mouth thoroughly with water to remove the acid from the tooth surfaces. The teeth are again isolated with cotton rolls and again thoroughly dried. The pit and fissure sealant prepared according to the foregoing description is then applied by conventional techniques.

From the foregoing description, it is apparent that the objects of this invention have been achieved in a new and novel manner. While only specific embodiments have been illustrated, it should be apparent from the foregoing description to those skilled in the art that other alternatives can be practiced within the spirit and the scope of the present invention.

What is claimed is:

1. An adhesive composition comprising a cement portion and a catalyst portion, the cement portion comprising from 5 to 95% by weight of a monomeric ester of an α-cyanoacrylic acid and from 95 to 5% by weight of a difunctional monomer diester of an acid from the group consisting of acrylic and methacrylic acid and a polyfunctional alcohol having at least two esterifiable hydroxy groups, and the catalyst portion comprising from about 2 to 15 parts by weight of a free radical catalyst for each hundred parts by weight of the total cement portion, and an amine activator therefor in the amount of from 5 to 150 mole percent of the free radical catalyst.

2. An adhesvie composition according to claim 1 wherein the monomeric ester of α-cyanoacrylic acid is of the formula

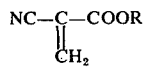

where R is a straight or branched chain alkyl group of from 1 to 16 carbon atoms, cyclohexyl and phenyl.

3. A composition according to claim 1 wherein the difunctional monomer is of the formula

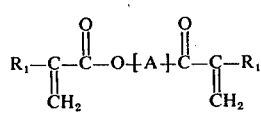

wherein $R_1$ is methyl or hydrogen and A is $-(R_2-O)_n-$ where $R_2$ is methylene, propylene, isopropylene, butylene, and isobutylene, and n is an integer of from 1 to 3, or

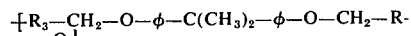

wherein $R_3$ are $-(CH_2-CH)-$ and

4. A composition according to claim 1 wherein the cement portion comprises from about 10 to 80% of the ester of α-cyanoacrylic acid and from about 80 to 10% of the difunctional monomer.

5. A composition according to claim 1 wherein said free radical catalyst is an organo-peroxide.

6. A composition according to claim 5 wherein said free radical catalyst is benzoyl peroxide.

7. A composition according to claim 1 wherein the amine activator is an amine having a $pK_b$ in water of from 1 to 12.

8. A composition according to claim 7 wherein the amine is selected from the group consisting of N,N-dimethyl-p-toluidine; N,N-dimethylaniline, N,N-diethylaniline, N-methylbenzylamine, triethanolamine, diethanolamine, 2-picoline, 4-picoline, tributylamine, 4-ethylpyridine, pyridine, N,N-diethyl-1-naphthylamine, hexamethylenediamine, N,N-diethylethylenediamine, N,N-dimethyl-p-toluidine, N,N-dimethylaniline, and N,N-di-β-hydroxyethyl-p-toluidine.

9. A composition according to claim 1 wherein said ester of α-cyanoacrylic acid is selected from the group consisting of isobutyl-2-cyanoacrylate; methyl-2-cyanoacrylate; ethyl-2-cyanoacrylate; propyl-2-cyanoacrylate; n-butyl-2-cyanoacrylate; n-amyl-2-cyanoacrylate; isoamyl-2-cyanoacrylate; n-hexyl-2-cyanoacrylate; n-heptyl-2-cyanoacrylate; and n-octyl-2-cyanoacrylate.

10. A composition according to claim 1 wherein the difunctional monomer is selected from the group consisting of 1,3-ethyleneglycol dimethacrylate; bisphenol A diglycidyl dimethacrylate; 1,3-butyleneglycol diacrylate; ethyleneglycol dimethacrylate; ethyleneglycol diacrylate; diethyleneglycol dimethacrylate; diethyleneglycol diacrylate; 1,3-propanediol dimethacrylate; 1,3-propanedial diacrylate; 2,2-dimethyl propanediol diacrylate; tripropyleneglycol dimethacrylate; tripropyleneglycol diacrylate; triethyleneglycol diacrylate; and triethyleneglycol dimethacrylate.

11. A composition according to claim 1 wherein said free radical catalyst is present in an amount of from 3 to 8% by weight of the cement portion.

12. A composition according to claim 1 wherein said amine activator is N,N dimethyl-p-toluidine and is present in substantially an amount of 100 mole percent as based on the moles of free radical catalyst.

13. A composition according to claim 1 wherein there is included a filler.

14. A composition according to claim 13 wherein the filler is from 1 to 4 parts by weight per each part by weight of the combined cement and catalyst portions.

15. A composition according to claim 13 in which said filler is selected from the group consisting of alumina, quartz and fused silica.

16. A composition according to claim 13 wherein the filler carries an undercoat of a trialkoxysilyl compound.

17. A composition according to claim 16 wherein the coated filler carries a coating of an amine activator.

18. A composition according to claim 1 wherein there is included from 5 to 25% by weight of sodium fluoride.

19. A composition according to claim 4 in which the ester of α-cyanoacrylic acid is isobutyl-2-cyanoacrylate, the difunctional monomer is 1,3-butyleneglycol dimethacrylate, the free radical catalyst is benzoyl peroxide, and the amine activator for the free radical catalyst is N,N-di-β-hydroxyethyl-p-toluidine.

20. A system for obtaining a hard cohesive cross-linked mass having distributed between a first component and a second component thereof a cement portion comprising from 5 to 95% by weight of a monomeric ester of an α-cyanoacrylic acid and from 95 to 5% by weight of a difunctional monomer diester of an acid from the group consisting of acrylic and methacrylic acid and a polyfunctional alcohol having at least two esterifiable hydroxy groups, and a catalyst portion comprising a free radical catalyst in the amount of from 2 to 15 parts by weight for each hundred parts by weight of the total cement portion, and an amine activator in the amount of from 5 to 150 mole percent of the free radical catalyst wherein all the amine activator is in the first component, and all the monomeric ester of the α-cyanoacrylic acid is in the second component.

21. A system according to claim 20 wherein the monomeric ester of α-cyanoacrylic acid is of the formula

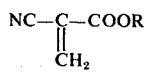

where R is a straight or branched chain alkyl group of from 1 to 16 carbon atoms, cyclohexyl and phenyl.

22. A system according to claim 20 wherein the difunctional monomer is of the formula

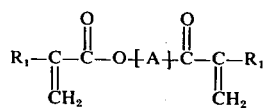

wherein $R_1$ is methyl or hydrogen and A is $-R_2\text{-O}]_n$ where $R_2$ is methylene, propylene, isopropylene, butylene, and isobutylene, and $n$ is an integer of from 1 to 3, or

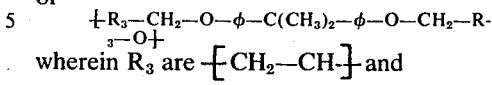

wherein $R_3$ are $\{CH_2-CH\}$ and

23. A system according to claim 20 wherein there is included a filler in an amount of from 1 to 4 parts by weight per each part by weight of the combined cement and catalyst portions.

24. A system according to claim 20 wherein the first component comprises the amine activator and the difunctional monomer; and the second component comprises the free radical catalyst and the monofunctional monomer.

25. A system according to claim 20 wherein the first component comprises the amine activator, the free radical catalyst, and the difunctional monomer; and the second component comprises the monofunctional monomer.

26. A system according to claim 20 wherein the first component comprises the amine activator and the free radical catalyst; and the second component comprises the monofunctional monomer and the difunctional monomer.

* * * * *

UNITED STATES PATENT AND TRADEMARK OFFICE
CERTIFICATE OF CORRECTION

PATENT NO. : 3,940,362
DATED : February 24, 1976
INVENTOR(S) : Wendell C. Overhults It is certified that error appears in the above-identified patent and that said Letters Patent are hereby corrected as shown below:

In the Abstract, line 5, "group" should read --- groups ---.

In Column 2, line 7, "usually" should be capitalized.

In Column 2, line 52, "aehesive" should read --- adhesive ---.

In Column 3, line 30, the formula should read --- $[\overline{R_2}\text{-}\overline{S}]_n$ In Column 4, line 38, "otherwise" should be capitalized.

In Column 5, line 35, "it" should be capitalized.

In Column 6, line 60, "if" should be capitalized.

In Column 7, line 12, "and" should be inserted between "pit" and "fissure".

In Column 8, line 23, "p" should be underscored.

In Column 8, line 36, "p" should be underscored.

In Column 12, line 1, formula should read --- $[\overline{R_2}\text{-}O\overline{]}_n$ Signed and Sealed this Fifteenth Day of February 1977

[SEAL]

Attest:

RUTH C. MASON
*Attesting Officer*

C. MARSHALL DANN
*Commissioner of Patents and Trademarks*